United States Patent [19]

Rosin

[11] 4,074,397
[45] Feb. 21, 1978

[54] DEVICE FOR SECURING CORDS, TUBES, AND THE LIKE

[76] Inventor: Stanley A. Rosin, 115 S. Indian Ave., Palm Springs, Calif. 92262

[21] Appl. No.: 732,725

[22] Filed: Oct. 15, 1976

[51] Int. Cl.$^2$ .......................................... A61M 25/02
[52] U.S. Cl. ............................. 24/73 AS; 24/73 SA; 128/DIG. 15; 128/DIG. 26
[58] Field of Search .............. 24/204, 73 VA, 73 SA, 24/3 R, DIG. 11, DIG. 18, 75 AS; 128/287, DIG. 15, 348, 133, DIG. 26, 349 R

[56] References Cited

U.S. PATENT DOCUMENTS

| | | | |
|---|---|---|---|
| 2,744,526 | 5/1956 | Saylors | 128/133 |
| 3,146,778 | 9/1964 | Krawiec | 24/73 SH |
| 3,430,300 | 3/1969 | Doan | 24/DIG. 11 |
| 3,472,198 | 10/1969 | Rinecker | 24/204 X |
| 3,543,977 | 12/1970 | Lockridge | 24/204 X |
| 3,583,057 | 6/1971 | Kolozsuary | 24/204 X |
| 3,677,250 | 7/1972 | Thomas | 24/DIG. 11 |
| 3,686,718 | 8/1972 | Brumlik | 24/204 |
| 3,765,421 | 10/1973 | Poprik | 128/DIG. 26 |
| 3,834,380 | 9/1974 | Boyd | 128/133 |
| 3,878,849 | 4/1975 | Muller et al. | 128/DIG. 26 X |

Primary Examiner—Werner H. Schroeder
Assistant Examiner—Moshe I. Cohen
Attorney, Agent, or Firm—Keith D. Beecher

[57] ABSTRACT

A disposable device is provided for securing cords and tubes during surgical, or other medical operations or medical services, or the like, by which cords and/or tubes extending to or from the patient may be conveniently fastened, for example to the paper or fabric sheet covering the patient during surgery, to the bedside railings or to the patient directly during intravenous injections or drainage, and so on. The device of the invention comprises a thin flexible pad having a pressure-sensitive adhesive layer on one side so that it may be removably attached to the aforesaid sheet, bed-rail or the like, and it also has an elongated flexible strip portion attached to, or integral with the pad, having a velcro element affixed to its distal end. In use, the pad is adhesively attached to a convenient supporting surface, such as described above, and the strip is wrapped around the tube or cord to be secured by the device. The velcro element is then pressed into the pad itself, or into a tab attached to the pad, the pad or tab being made of fabric suitable for receiving the velcro element in fastening relationship therewith. The device, in this manner, serves as an appropriate means for securely holding the tube or cord and for anchoring the tube or cord to the appropriate supporting surface.

3 Claims, 4 Drawing Figures

DEVICE FOR SECURING CORDS, TUBES, AND THE LIKE

BACKGROUND OF THE INVENTION

Many types of surgery require a multiplicity of tubes and/or electric wires and cords to be inserted into the patient, or attached to electrodes on the patient. Problems have arisen in the past in providing adequate means for securing such tubes and cords so that they may be firmly held during the operation in positions in which they will not interfere with the surgeon, anesthetist or attendant nurses.

The improved disposable device of the present invention, as will become more evident as the present description proceeds, finds particular utility for anchoring such tubes and cords during surgical operations, and the like, to appropriate support surfaces, such as described above.

A special feature of the device is that the tube or cord may be adjusted, removed or replaced, without removing the device from the supporting surface, thereby avoiding any discomfort to the patient should the device, for example, be attached directly to his body. As will also become evident, as the description proceeds, the clamping device of the invention also finds utility in securing tubes, for example, to the rail of the bed during intravenous injections. In fact, the clamping device of the invention has wide utility in medical and non-medical fields wherever it is desired to secure wires, tubes, cords, and the like, temporarily to an appropriate support surface.

As described briefly above, the device of the invention, comprises a thin flexible pad having a pressure-sensitive adhesive on one side, so that the pad may be adhesively secured to a supporting surface. An elongated flexible strip is attached to the pad, or formed integral therewith, as will be described, and a VELCRO tab is affixed to the end of the strip. In operation, the strip is wrapped around the tube or cord to be supported by the device, and the Velcro tab at its distal end is pressed into the pad, or into an appropriate fabric member on the pad, so that the VELCRO tab may be engaged in a fastening relationship.

VELCRO fasteners per se, are known to the art. These fasteners comprise two strips of material, one being a Velcro tab provided with a multiplicity of small plastic hooks, and the other being a thread-like fabric such as a loop spun nylon. The hooks of the Velcro pad engage or seize the loops of the fabric strip when the two strips are brought together, so as to form a firm bond. The fastener can be opened by manually peeling one strip away from the other.

The VELCRO fastener described above is used in the clamping device of the present invention, in combination with the other elements described above, so as to provide an improved securing device which has wide utility, which can be produced inexpensively, and sold at a low cost, and which is readily disposable.

DETAILED DESCRIPTION OF THE ILLUSTRATED EMBODIMENT

Figure 1:
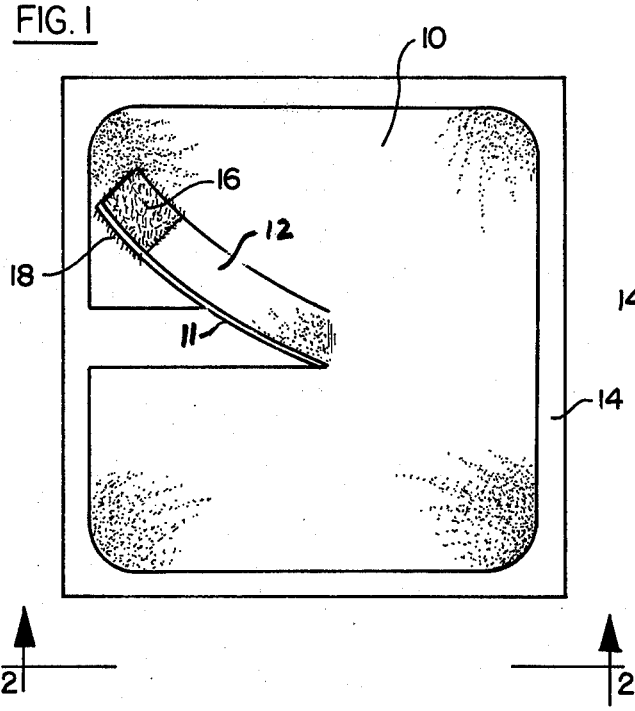
FIG. 1 is a plan view of a presently preferred embodiment of the invention.

The securing device shown in FIG. 1 includes a thin flexible fabric pad 10 which may, for example, be composed of loop spun nylon, or other appropriate fabric. A pressure-sensitive adhesive layer 11 (FIG. 2) is placed on one surface of the fabric layer 10, and an appropriate backing paper 14 is placed over the pressure-sensitive adhesive layer.

A portion of the fabric pad 10 is cut out to form an elongated flexible strip 12, hinged near the center of the pad, the strip being integral with the fabric. A pair or a folded single piece of VELCRO tabs 16 and 18 are affixed to the end of strip 12, on each side of the strip, as best shown in FIG. 2.

Figure 2:
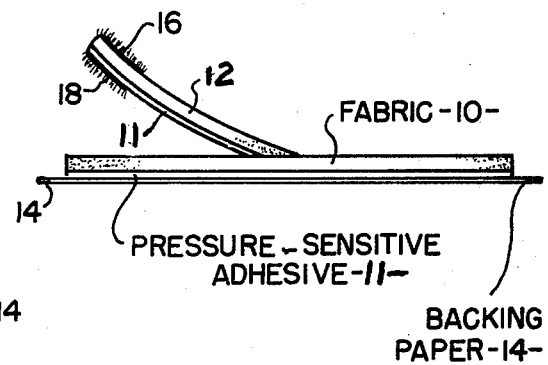
FIG. 2 is a end view of the embodiment of FIG. 1, taken along the lines 2—2 of FIG. 1.
Figure 3:
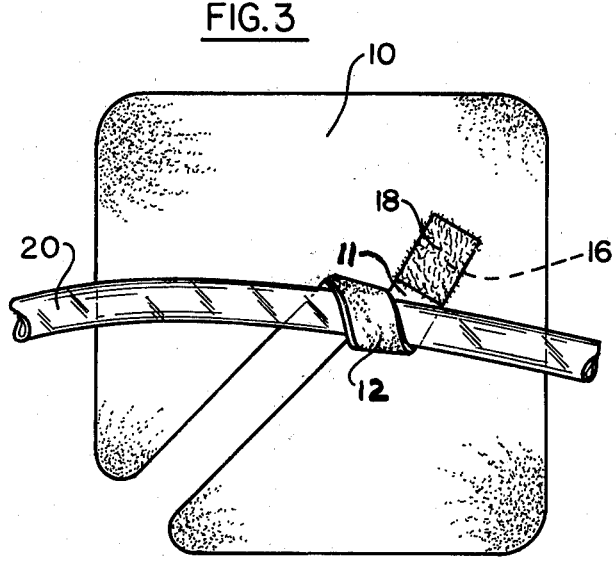
FIG. 3 shows the embodiment of FIG. 1, as used to anchor a tubular member in a non-slipping engagement.

In FIG. 3, the securing device of FIGS. 1 and 2 is used to clamp a tube in a non-slipping manner. For that purpose the strip 12 is wrapped around the tube, as shown, so that the inner adhesive face of the strip engages the surface of the tube to hold the tube from slipping.

Figure 4:
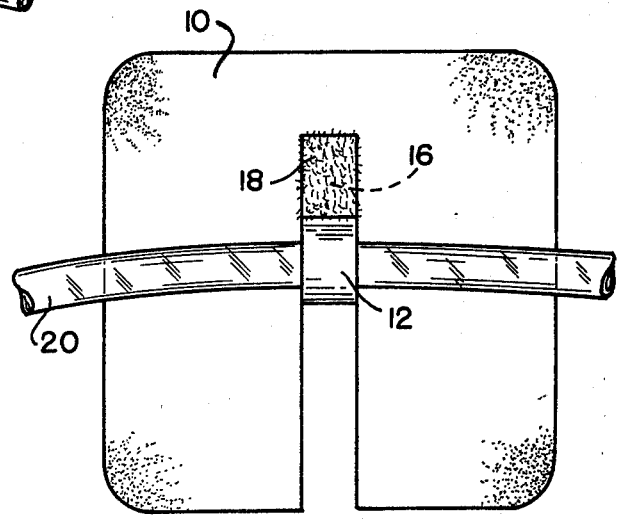
FIG. 4 shows the embodiment of FIG. 1, as used to anchor a tubular member in a slipping engagement therewith.

In the embodiment of FIG. 4, the strip 12 is wrapped around the tube in a manner such that its outer fabric face engages the tube, so that the tube is free to slip in the loop formed by the strip and pad.

It will be understood, of course, that while a particular embodiment of the invention has been shown and described, modifications may be made. It is intended to cover all modifications which come within the true spirit and scope of the invention in the following claims.

What is claimed is:

1. A device for securing cords, tubes and the like to a supporting surface comprising: a flexible fabric pad and having a pressure-sensitive adhesive layer on one surface thereof; an elongated flexible fabric strip member formed as a cut-out portion of said pad also having the pressure-sensitive adhesive layer on one surface thereof, said strip member having one end integral with said pad and having a distal end; a first tab having a multiplicity of minute hook members formed thereon, said first tab being affixed to the distal end of said strip member on one side thereof; a second tab having a multiplicity of minute hook members formed thereon, said second tab being affixed to the distal end of said strip member on the other side thereof; said flexible fabric being a material capable of receiving the hook members of the tabs in fastening relationship therewith when the tabs are selectively pressed against the pad after the strip member has been looped around a tube, cord, or the like, to be secured by the device.

2. The device defined in claim 1, in which said pad has a square configuration, and said cut-out portion extends angularly to one corner of the pad.

3. The device defined in claim 1, in which said pad has a square configuration and said cut-out portion extends transversely from an internal location on the pad to one edge thereof.

* * * * *